United States Patent
Kaeppeli et al.

(10) Patent No.: US 10,359,442 B2
(45) Date of Patent: Jul. 23, 2019

(54) SAMPLE CONTAINER CARRIER

(71) Applicant: Roche Diagnostics Operations, Inc., Indianapolis, IN (US)

(72) Inventors: Marcel Kaeppeli, Merenschwand (CH); Pius Hermann, Urswil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/434,522

(22) Filed: Feb. 16, 2017

(65) Prior Publication Data
US 2017/0248623 A1 Aug. 31, 2017

(30) Foreign Application Priority Data

Feb. 25, 2016 (EP) ..................................... 16157464

(51) Int. Cl.
*G01N 35/04* (2006.01)
*B01L 9/06* (2006.01)
*B01L 3/00* (2006.01)

(52) U.S. Cl.
CPC ............ *G01N 35/04* (2013.01); *B01L 3/5453* (2013.01); *B01L 9/06* (2013.01); *B01L 2200/025* (2013.01);
(Continued)

(58) Field of Classification Search
CPC .................................. G01N 35/04; B01L 9/06
(Continued)

(56) References Cited

U.S. PATENT DOCUMENTS

| 5,014,868 A | 5/1991 | Wittig et al. |
| 5,224,585 A | 7/1993 | Blanco et al. |

(Continued)

FOREIGN PATENT DOCUMENTS

| EP | 0414644 | * | 2/1991 |
| EP | 0414644 A2 | | 2/1991 |

(Continued)

OTHER PUBLICATIONS

Search Report dated Aug. 24, 2016, in Application No. EP 16157464, 8 pages.

*Primary Examiner* — Jill A Warden
*Assistant Examiner* — Jacqueline Brazin
(74) *Attorney, Agent, or Firm* — Roche Diagnostics Operations, Inc.

(57) ABSTRACT

A sample container carrier for transporting sample containers, for example test tubes and/or vials, in a laboratory automation system is presented. The sample container carrier comprises a body having a hollow center with a central axis. The hollow center accommodates a lower end of a sample container. The sample container carrier also comprises three resiliently deformable and/or displaceable first retaining elements mounted to the body. The first retaining elements, distributed about the central axis, clamp a sample container inserted in the hollow center. The sample container carrier also comprises three resiliently deformable and/or displaceable second retaining elements mounted to the body. The second retaining elements, distributed about the central axis, clamp the sample container inserted in the hollow center underneath the three first retaining elements. The second retaining elements are arranged at least partly inside the hollow center.

13 Claims, 3 Drawing Sheets

(52) U.S. Cl.
CPC .. *B01L 2200/18* (2013.01); *G01N 2035/0401* (2013.01); *G01N 2035/0406* (2013.01)

(58) Field of Classification Search
USPC ........................................................ 422/547
See application file for complete search history.

(56) References Cited

U.S. PATENT DOCUMENTS

| | | |
|---|---|---|
| 5,350,564 A | 9/1994 | Mazza et al. |
| 5,651,941 A | 7/1997 | Stark et al. |
| 5,720,377 A | 2/1998 | Lapeus et al. |
| 5,744,367 A | 4/1998 | Talley et al. |
| 6,045,319 A | 4/2000 | Uchida et al. |
| 6,074,612 A | 6/2000 | Sagstetter |
| 6,274,092 B1 | 8/2001 | Itoh |
| 6,343,690 B1 | 2/2002 | Britton et al. |
| 6,571,934 B1 | 6/2003 | Thompson et al. |
| 6,971,506 B2 * | 12/2005 | Hassinen ............ G01N 35/04 198/803.14 |
| 7,485,264 B2 | 2/2009 | Itoh |
| 8,147,778 B2 | 4/2012 | Pedrazzini |
| 2003/0143120 A1 | 7/2003 | Ruediger et al. |
| 2005/0180896 A1 | 8/2005 | Itoh |
| 2010/0155427 A1 | 6/2010 | Lilienthal et al. |
| 2010/0186618 A1 | 7/2010 | King et al. |
| 2010/0226828 A1 * | 9/2010 | Itoh ........................ B01L 9/06 422/562 |
| 2012/0118903 A1 * | 5/2012 | Norton ................ B01L 3/0293 220/755 |
| 2012/0295358 A1 | 11/2012 | Ariff et al. |
| 2013/0027185 A1 | 1/2013 | Lavi |
| 2014/0234065 A1 | 8/2014 | Heise et al. |
| 2014/0301916 A1 | 10/2014 | Ohga et al. |
| 2015/0101911 A1 * | 4/2015 | Friedman ............ G01N 35/04 198/617 |
| 2017/0131310 A1 | 5/2017 | Volz et al. |
| 2017/0248624 A1 | 8/2017 | Kaeppeli et al. |

FOREIGN PATENT DOCUMENTS

| | | |
|---|---|---|
| EP | 0916406 A2 | 5/1999 |
| EP | 2589966 A1 | 5/2013 |
| EP | 2799884 A1 | 11/2014 |
| EP | 2988134 A1 | 2/2016 |
| GB | 11486 A | 5/1911 |
| WO | 2011/138448 A1 | 11/2011 |
| WO | 2013/064656 A1 | 5/2013 |
| WO | 2014/138533 A1 | 9/2014 |

* cited by examiner

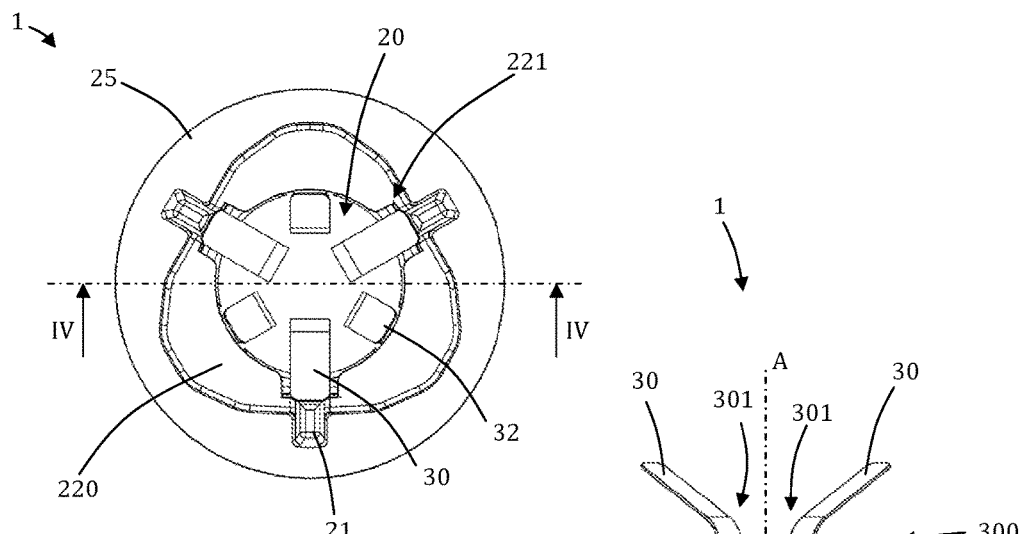
Fig. 3
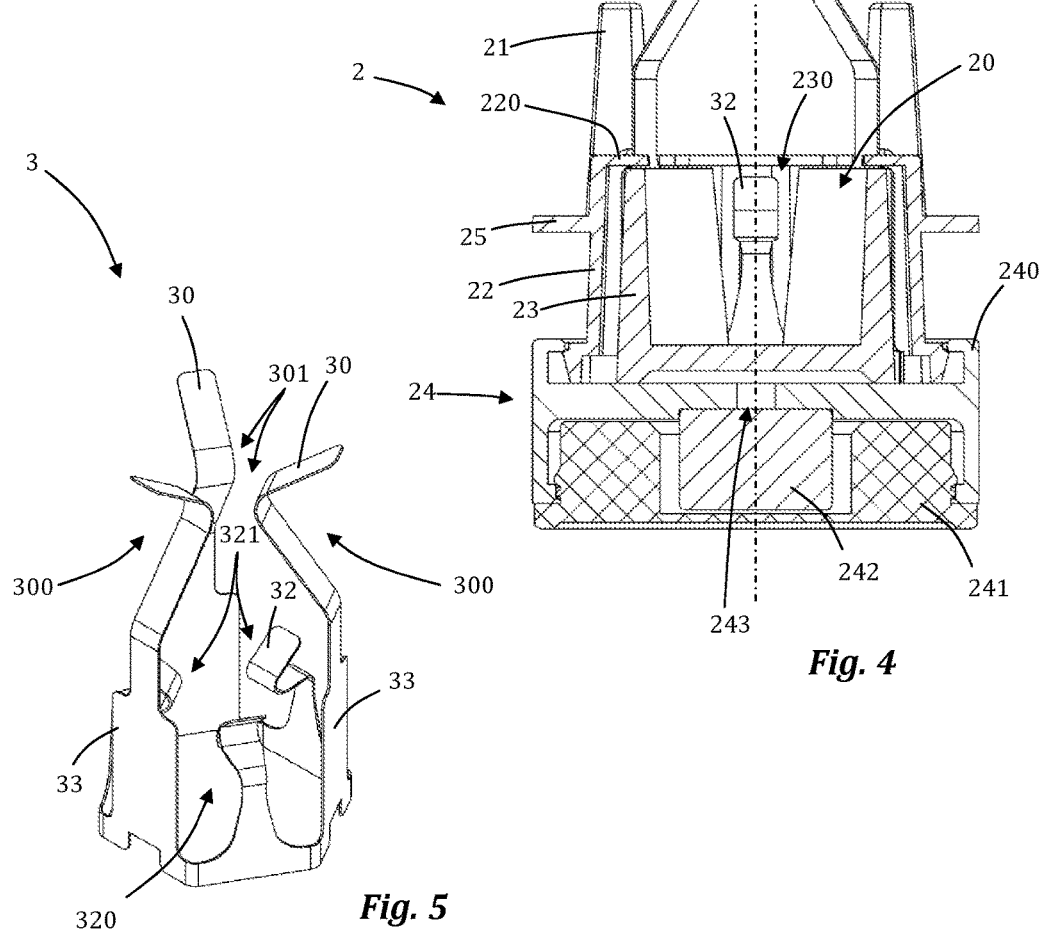
Fig. 4
Fig. 5

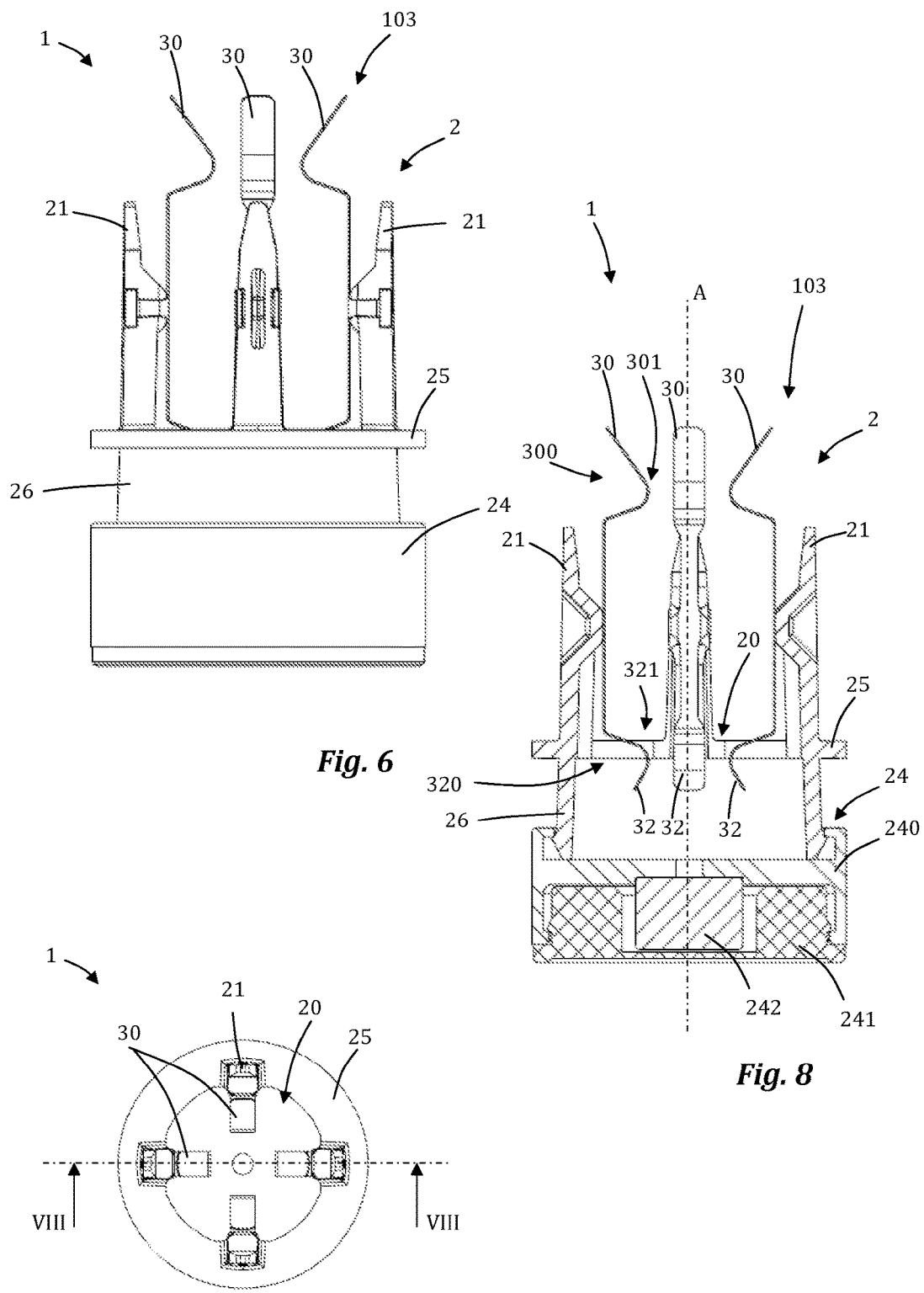

US 10,359,442 B2

SAMPLE CONTAINER CARRIER

CROSS-REFERENCE TO RELATED APPLICATIONS

This application claims priority to EP 16157464.5, filed Feb. 25, 2016, which is hereby incorporated by reference.

BACKGROUND

The present disclosure relates to a sample container carrier for transporting sample containers, for example test tubes and/or vials, in a laboratory automation system. The invention further relates to a laboratory sample distribution system having a number of sample container carriers, and a laboratory automation system comprising a laboratory sample distribution system.

A laboratory automation system typically comprises a number of pre-analytical, analytical and/or post-analytical stations, in which samples, for example blood, saliva, swab and other specimens taken from the human body, are processed. It is generally known to provide various containers, such as test tubes or vials, containing the samples. The test tubes are also referred to as sample tubes. In the context of the application, containers such as test tubes or vials for containing a sample are referred to as sample containers.

Several sample containers can be placed in racks for a handling. In an alternative distribution system, sample containers are place in an upright or vertical position in sample container carriers, or pucks, having a retaining area for retaining sample containers.

Generally, in laboratory automation systems different kinds of sample containers are handled, in particular test tubes and/or vials of different diameters. It is further known to control the transport of the sample containers and/or a treatment of the sample contained in the sample container by a bar code provided on an outside surface of the sample container. For this purpose, the bar code should be readable during the transport and/or at all handling stations without the necessity to remove the sample container from the carrier.

Therefore, there is a need for a sample container carrier that allows for secure support of different types of sample containers without hindering a readability of the bar code or any other type of identification code provided on an outside of the tube.

SUMMARY

According to the present disclosure, a sample container carrier for transporting sample containers in a laboratory automation system is presented. The sample container carrier can comprise a body having a hollow center with a central axis (A). The hollow center can be adapted to accommodate a lower end of a sample container. The sample container carrier can also comprise at least three first retaining elements mounted to the body. The at least three first retaining elements can be resiliently deformable and/or displaceable. The first retaining elements can be distributed about the central axis (A) and adapted to clamp a sample container inserted in the hollow center of the body in an area above the hollow center. The sample container carrier can also comprise at least three second retaining elements mounted to the body. The at least three second retaining elements can be resiliently deformable and/or displaceable. The second retaining elements can be distributed about the central axis (A) and adapted to clamp the sample container inserted in the hollow center of the body underneath the at least three first retaining elements. The second retaining elements can be arranged at least partly inside the hollow center of the body.

Accordingly, it is a feature of the embodiments of the present disclosure to provide for a sample container carrier that allows for secure support of different types of sample containers without hindering a readability of the bar code or any other type of identification code provided on an outside of the tube. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 3 illustrates a top view of the sample container carrier of FIG. 1 according to an embodiment of the present disclosure.

FIG. 4 illustrates a sectional view along line IV-IV of the sample container carrier of FIG. 3 according to an embodiment of the present disclosure.

FIG. 5 illustrates a retaining structure of the sample container carrier of FIG. 1 according to an embodiment of the present disclosure.

FIG. 6 illustrates a side view of a second embodiment of a sample container carrier for transporting sample containers according to an embodiment of the present disclosure.

FIG. 7 illustrates a top view of the sample container carrier of FIG. 6 according to an embodiment of the present disclosure.

FIG. 8 illustrates a sectional view along line VIII-VIII of the sample container carrier of FIG. 7 according to an embodiment of the present disclosure.

DETAILED DESCRIPTION

Figure 1:
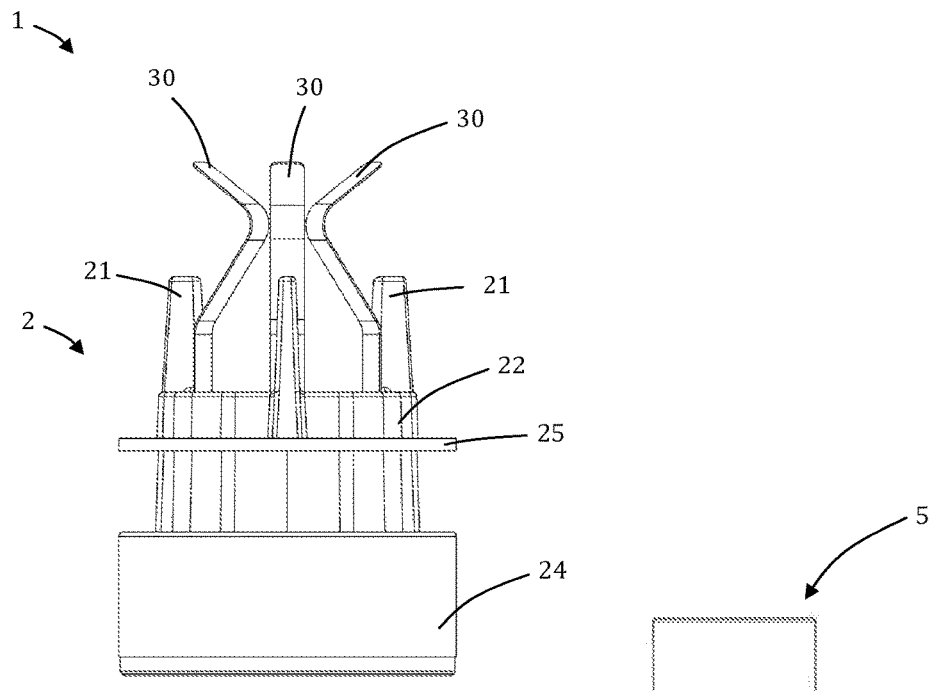
FIG. 1 illustrates a side view of a sample container carrier for transporting sample containers according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample container carrier for transporting sample containers in a laboratory automation system is provided. The sample container carrier can comprise a body having a hollow center with a central axis. The hollow center can be adapted to accommodate a lower end of a sample container. The sample container carrier can comprise at least three resiliently deformable and/or displaceable first retaining elements mounted to the body. The first retaining elements can be distributed about the central axis and adapted to clamp a sample container inserted in the hollow center of the body in an area above the hollow center. The sample container carrier can comprise at least three resiliently deformable and/or displaceable second retaining elements mounted to the body. The second retaining elements can be distributed about the central axis and adapted to clamp the sample container inserted in the hollow center of the body underneath the at least three first retaining elements. The second retaining elements can be arranged at least partly inside the hollow center of the body.

Sample containers of different sizes, in particular of different diameters, can be securely held or at least supported at a bottom region by the second retaining elements arranged at least partly inside the hollow. Hence, a sample container can be prevented from tipping even in the case where the sample container is not fully inserted and does not reach a maximum depth inside the hollow center. By the first and the second retaining elements, the sample containers can be clamped at two distinct clamping areas at different heights. By arranging the second retaining elements at least partly inside the hollow center, a distance between the clamping areas can be maximized without increasing the overall size of the sample container carriers.

In one embodiment, the first retaining elements and the second retaining elements can be arranged in an alternating sequence about the central axis. As the second retaining elements are arranged inside the hollow, the second retaining elements may not hinder the visibility and/or readability of a bar code provided on the sample container. The number of first and second retaining elements can differ, in one embodiment, wherein for example, two second retaining elements can be arranged between two first retaining elements. In some embodiments, the number of first and second retaining elements can be the same and the elements can be equally spaced about the central axis.

In the alternative, or in addition, the first retaining elements and the second retaining elements can be arranged so that in each case, one first retaining element and one second retaining element can be aligned in a direction substantially parallel to the central axis.

The first and the second retaining elements can be resiliently deformable and/or displaceable. In one embodiment, the body can be provided with a number of upwardly projecting support fingers for supporting the first retaining elements in a direction radially outwards about the central axis. By the support fingers, a stiffness of the clamping device formed by the first retaining elements can be increased and a maximum deformation and/or displacement radially outwards can be limited.

In one embodiment, the first retaining elements and/or the second retaining elements can each be made of sheet metal material. Suitable sheet metal material can be chosen by the person skilled in the art. In one embodiment, the first retaining elements and/or the second retaining elements can each comprise a hooked portion having a vertex directed toward the central axis. The hooked portion can allow for a reliable clamping. Further, the legs of the hooked portion can also function as guidance upon insertion of the sample containers.

In one embodiment, a retaining structure formed integrally from sheet metal material can be provided, in which a retaining structure can include the first retaining elements and the second retaining elements. In other words, the number of elements and, thus, the assembly effort can be reduced.

For mounting the retaining structure to the body, in one embodiment, the body can comprise at least two parts, an outer sleeve and an inner sleeve received in the outer sleeve. The retaining structure can be mounted between the outer sleeve and the inner sleeve. If, in this case, further upwardly projecting support fingers for supporting the first retaining elements can be provided. The support fingers, in one embodiment, can be formed integrally with the outer sleeve.

In one embodiment, at least one of the outer sleeve and the inner sleeve can be provided with a protruding edge forming a stop for the retaining structure. The protruding edge can protrude in some embodiments substantially perpendicular to the central axis from an upper rim of the outer sleeve radially to the inside or from an upper rim of the inner sleeve radially to the outside.

In one embodiment, the outer sleeve or the inner sleeve can be formed integrally with a sliding disc. In one embodiment, the body can further comprise a sliding disc. The outer sleeve and the inner sleeve can be mounted to the sliding disc. The sliding disc can accommodate, for example, a magnetically active element. The at least one magnetically active element can be adapted to interact with a magnetic field such that a driving force can be applied to the sample container carrier. For instance, at least one permanent magnet can be provided as the magnetically active device.

In an alternative embodiment, a number of retaining strips formed from sheet metal material can be provided where each retaining strips can comprise one of the first retaining element and one of the second retaining elements. The retaining strips, in some embodiments, can be identical in design. For a simple assembly, the retaining strips can be clipped and/or glued to the body.

In one embodiment, the body can be provided with a number of upwardly projecting support fingers. The retaining strips can be attached, in one embodiment clipped, to the support fingers. The fixation area at which the retaining strips are attached to the support fingers can be chosen suitably by the person skilled in the art. The chosen fixation area can influence the maximum deformation and/or displacement of the first and the second retaining elements. In one embodiment, the fixation area can be chosen at least essentially mid-way between the first and the second retaining element of each retaining strip.

In order to allow for a simple assembly, the body, in one embodiment, can comprise a sleeve surrounding the hollow center and a sliding disc. The sleeve can be mounted to the sliding disc. In particular, the sleeve can be mounted to the sliding disc using a separable connection, such as a snap-fit connection or a screw connection, or a non-separable connection for example by gluing or welding.

A laboratory sample distribution system having a number of sample container carriers is provided. The distribution system, for example, can comprise a transport plane with a number of magnetic actuators for generating a magnetic field such that a driving force is applied to each of the sample container carriers for transporting the sample container carriers. Such a system is described for example in WO 2013/064656 A1 and is incorporated herein by reference. The distribution system, in alternative or in addition, in one embodiment, can comprise additional conveyor devices for moving a sample container carrier along a defined path.

A laboratory automation system with a number of pre-analytical, analytical and/or post-analytical stations, and with a distribution system having a number of sample container carriers is provided.

Figure 2:
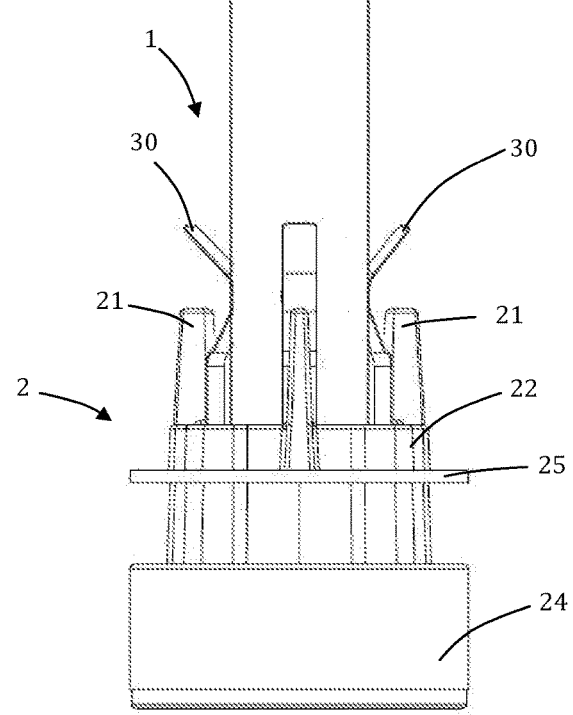
FIG. 2 illustrates the sample container carrier of FIG. 1 retaining a sample container according to an embodiment of the present disclosure.

FIGS. 1 to 4 show a first embodiment of a sample container carrier 1 for transporting sample containers 5 (see FIG. 2). FIG. 5 shows a retaining structure 3 of the sample container carrier 1.

The sample container carrier 1 shown in FIGS. 1 to 4 can comprise a body 2 having a hollow center 20 with a central axis A, three resiliently deformable and displaceable first retaining elements 30 mounted to the body 2, and three resiliently deformable and displaceable second retaining elements 32 also mounted to the body 2.

The body 2 can further comprise a sliding disc 24. The sliding disc 24 can comprise two coupled elements 240, 241 accommodating in-between a magnetically active element 242, which can be adapted to interact with a magnetic field such that a driving force can be applied to the sample container carrier 1. Due to production-related issues, in the embodiment shown, the upper element 51 of the sliding disc 5 can be provided with a hole 53. In other embodiments, no such hole is provided.

As best seen in FIG. 2, the hollow center 20 can be adapted for accommodating a lower end of a sample container 5. The sample container 5 can be clamped by the first and the second retaining elements 30, 32 at two different heights.

As best seen in FIG. 4, the second retaining elements 32 can be arranged inside the hollow center 20 of the body 2 for clamping the for transporting sample containers 5 at the lower end close to its bottom.

In the embodiment shown, an equal number of first and second retaining elements 30, 32 can be provided, namely three first retaining elements 30 and three second retaining elements 32, which can be distributed about the central axis A in an alternating sequence. The body 2 can be provided with a number of upwardly projecting support fingers 21 for supporting the first retaining elements 30 in a radial outward direction about the central axis A. The retaining elements 30 may not be fixed to the support fingers 21 and moveable towards the center axis A relative to the support fingers 21.

The first retaining elements 3 and the second retaining elements 32 can each be made of sheet metal material.

More particular, in the embodiment shown in FIGS. 1 to 5, a retaining structure 3 formed integrally from sheet metal material can be provided, in which the retaining structure 3 can include the first retaining elements 30 and the second retaining elements 32. The retaining structure 3 is shown in detail in FIG. 5. For forming the retaining structure 3, sheet metal material can be bent into a hexagon. The first retaining elements 30 and the second retaining elements 32 can be provided at side surfaces of the hexagon. As best seen in FIGS. 4 and 5, the first retaining elements 30 and the second retaining elements 32 can each comprise a hooked portion 300, 320 having a vertex 301, 321 directed toward the central axis A. The retaining structure 3 can further comprise flat mounting surfaces 33.

The body 2 of the embodiment shown in FIGS. 1 to 5 can comprise an outer sleeve 22 and an inner sleeve 23 received in the outer sleeve 22. The retaining structure 3 can be mounted between the outer sleeve 22 and the inner sleeve 23. For a positioning of the retaining structure 3 along the direction of the central axis A, the outer sleeve 22 can be provided with a protruding edge 220 forming a stop for the retaining structure 3. At the opposite end, the outer sleeve 22 and the inner sleeve 23 can be mounted to the sliding disc 24 such that retaining structure 3 can be fixed in position along the direction of the central axis A between the protruding edge 220 of the outer sleeve 22 and the sliding disc 24. The protruding edge 220 can be provided with cutouts 221 (see FIG. 3) for the first retaining elements 30 allowing the first retaining elements 30 to extend upwardly past the protruding edge 220.

The hollow center 20 having a circular cross-section can be formed by the inner sleeve 23. Cutouts 230 (see FIG. 4) can be provided for the second retaining elements 32 allowing the second retaining elements 30 to protrude radially inside the inner sleeve 23. A bottom of the hollow center 20 can be flat. The inner shell surface of the inner sleeve 23 can be slightly tapered for guiding the sample container 5 upon the insertion towards the bottom and to allow for an easy demolding process when manufacturing the inner sleeve by injection molding.

The outer sleeve 22 can be provided with a rim 25. The sliding disc 24 together with the rim 25 can form a guide groove allowing movement of the sample container carrier 1 with or without sample container 5 along a rail (not shown) or a similar element. Further, in the embodiment shown in FIGS. 1 to 5, an outer shell surface of the outer sleeve 22 can be non-circular to allow for an easier gripping of the sample container carrier 1.

FIGS. 6 to 8 show a second embodiment of a sample container carrier 1 comprising a body 2, four resiliently deformable and displaceable first retaining elements 30 mounted to the body 2, and four resiliently deformable and displaceable second retaining elements 32 also mounted to the body 2.

In the embodiment shown in FIGS. 6 to 8, the first retaining elements 30 and the second retaining elements 32 can be arranged such that in each case one first retaining element 30 and one second retaining element 32 can be aligned in a direction substantially parallel to the central axis A. More particular, a number of retaining strips 103 each formed from sheet metal material can be provided. Each retaining strip 103 can comprise one of the first retaining elements 30 and one of the second retaining elements 32.

The body 2 can comprise a sleeve 26 surrounding the hollow center 20, four upwardly projecting support fingers 21, and a sliding disc 24. The support fingers 21 can be formed integrally with the sleeve 26. The support fingers 21 can extend upwardly from an upper end of the sleeve 26. The conjoint element comprising the sleeve 26 and the support fingers 21 can be mounted to the sliding disc 24, in particular clipped to the sliding disc 24.

The retaining strips 103 can be attached to the support fingers 21 approximately at a region midway between hooked portions 300, 320 of the first and the second retaining elements 30, 32. The second retaining elements 32, in particular the hook portions 320 of the second retaining elements 32, can be arranged inside the sleeve 26. The vertices 301, 321 of the hooked portions 300, 320 can be directed toward the central axis A. It can be obvious to the person skilled in the art that a restoration force of the retaining elements 30, 32 can be influenced by properly choosing a length of the retaining strips 103 and/or the attachment area for attaching the retaining strips 103 to the support fingers 21. In alternative embodiments, the retaining strips 103 can be attached to the support fingers 21 at more than one area.

In the embodiment shown, the hooked portions 300 of the first retaining elements 30 can have a longer leg at the distal end for a reliable guidance of the sample container 5 (see FIG. 2) upon insertion into the sample container carrier 1.

In the embodiment shown in FIGS. 6 to 8, the hollow center 20 of the body 2 can be provided with an upward tapering portion. In other words, the diameter of the hollow center 20 can be increased towards a bottom of the hollow center 20. This can allow tilting of the sample containers 5 upon an insertion. However, due to the resilient restoring forces of the second retaining elements 32, the sample carrier (5 see FIG. 2) can be brought back into an upright position.

The sliding disc 24 of FIGS. 6 to 8 corresponds to that of FIGS. 1 to 4 and can also comprise two coupled elements 240, 241 accommodating a magnetically active element 242, which can be adapted to interact with a magnetic field such that a driving force can be applied to the sample container carrier 1. At an upper end of the sleeve 26, a rim 25 can be provided for forming a guiding groove together with the sliding disc 24.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A sample container carrier for transporting sample containers in a laboratory automation system, the sample container carrier comprising:
    a body having a hollow center with a central axis (A), wherein the hollow center is adapted to accommodate a lower end of a sample container, wherein the body comprises at least two parts, an outer sleeve and an inner sleeve received in the outer sleeve;
    a retaining structure formed integrally from bent sheet metal material, wherein the retaining structure comprises three first retaining elements mounted to the body, three second retaining elements mounted to the body, and a connecting band having a hexagonal contour with six side surfaces, wherein the three first retaining elements and the three second retaining elements are arranged in an alternating sequence about the central axis (A) at the six side surfaces of the connecting band, wherein the three first retaining elements are resiliently deformable and/or displaceable, wherein the first retaining elements are distributed about the central axis (A) and adapted to clamp a sample container inserted in the hollow center of the body in an area above the hollow center, wherein the three second retaining elements are resiliently deformable and/or displaceable, wherein the second retaining elements are distributed about the central axis (A) and adapted to clamp the sample container inserted in the hollow center of the body underneath the at least three first retaining elements, wherein the second retaining elements are arranged at least partly inside the hollow center of the body, and wherein the retaining structure is mounted between the outer sleeve and the inner sleeve.

2. The sample container carrier according to claim 1, wherein the body is provided with a number of upwardly projecting support fingers for supporting the first retaining elements in a direction radially outwards about the central axis (A).

3. The sample container carrier according to claim 1, wherein the first retaining elements and/or the second retaining elements each comprise a hooked portion having a vertex directed toward the central axis (A).

4. The sample container carrier according to claim 1, wherein the outer sleeve and/or the inner sleeve is provided with a protruding edge forming a stop for the retaining structure.

5. The sample container carrier according to claim 1, wherein the body further comprises a sliding disc.

6. The sample container carrier according to claim 5, wherein the outer sleeve and the inner sleeve are mounted to the sliding disc.

7. The sample container carrier according to claim 3, further comprising,
    a number of retaining strips formed from sheet metal material, each retaining strip comprising one of the first retaining elements and one of the second retaining elements.

8. The sample container carrier according to claim 7, wherein the body is provided with a number of upwardly projecting support fingers.

9. The sample container carrier according to claim 8, wherein the retaining strips are attached to the support fingers.

10. The sample container carrier according to claim 7, wherein the body comprises a sleeve surrounding the hollow center and a sliding disc.

11. The sample container carrier according to claim 10, wherein the sleeve is mounted to the sliding disc.

12. A laboratory sample distribution system having a number of sample container carriers according to claim 1.

13. A laboratory automation system with a number of pre-analytical, analytical and/or post-analytical stations and with a laboratory sample distribution system according to claim 12.

* * * * *